US007927584B2

(12) United States Patent
Allende

(10) Patent No.: US 7,927,584 B2
(45) Date of Patent: Apr. 19, 2011

(54) LACTIC BACTERIA USEFUL AS PROBIOTICS

(76) Inventor: Miguel Angel García Allende, Buenos Aires (AR)

( * ) Notice: Subject to any disclaimer, the term of this patent is extended or adjusted under 35 U.S.C. 154(b) by 718 days.

(21) Appl. No.: 11/700,127

(22) Filed: Jan. 31, 2007

(65) Prior Publication Data

US 2008/0063666 A1    Mar. 13, 2008

(30) Foreign Application Priority Data

Feb. 1, 2006    (AR) ................................. P060100370

(51) Int. Cl.
*A01N 63/00* (2006.01)
*A01N 65/00* (2006.01)
*A61K 39/02* (2006.01)

(52) U.S. Cl. ................. 424/93.1; 424/234.1; 424/235.1; 424/93.48

(58) Field of Classification Search .................. None
See application file for complete search history.

(56) References Cited

U.S. PATENT DOCUMENTS

| 5,951,977 | A  | * | 9/1999  | Nisbet et al. ................. | 424/93.3 |
| 7,132,102 | B2 | * | 11/2006 | Stern et al. ................. | 424/190.1 |
| 7,452,544 | B2 | * | 11/2008 | Stern et al. ................. | 424/282.1 |
| 7,459,289 | B2 | * | 12/2008 | Klaenhammer et al. ..... | 435/69.1 |
| 7,708,988 | B2 | * | 5/2010  | Farmer ....................... | 424/93.45 |
| 2008/0063666 | A1 | * | 3/2008 | Allende ..................... | 424/244.1 |

FOREIGN PATENT DOCUMENTS

EP    1816190 A1 *  8/2007

OTHER PUBLICATIONS

Zimmermann, Old Herborn University Smeinar Monograph, 2002, 15:69-94 abstract only.*
de Vos et al, Current Opinion in Biotechnology, 2004, 15:86-93.*
Millette et al, Letters in Applied Microbiology, 2007, 44:314-319.*
Linaje et al, J. Applied Microbiology, 2004, 96:761-771.*
Kayser, International J. Food Microbiology, 2003, 88:255-262.*
De Vuyst et al, International J. Food Microbiology, 2003, 84:299-318.*
Christensen, Dissertation Abstracts International, 2007, 69/7B:3913 abstract only.*
Gillor, Applied Microbiology Biotechnology, 2008, 81:591-606.*
Giraffe, International J. Food Microbiology, 2003, 88:215-222.*
Sparo et al, Food Microbiology, 2008, 25:607-615.*
Franz et al, International J. Food Microbiology, 2003, 88:105-122.*
Heller, Am. J. Clin. Nutr., 2001, 73(suppl):374S-379S.*
Basualdo et al, Annals Tropical Medicine and Parasitology, Sep. 2007, 101/6:559-562.*
Carlos et al, International J. Food Microbiology, 2009, 129:194-199.*
Goetz et al, J. Biochem. Biophys. Methods 60 (2004) 281-293.*

* cited by examiner

*Primary Examiner* — N. M Minnifield
(74) *Attorney, Agent, or Firm* — Arent Fox LLP

(57) ABSTRACT

An isolated strain of *Enterococcus faecalis* GALT deposited under number CECT 7121 of the group of lactic bacteria is disclosed, which is capable of surviving and colonizing the gastrointestinal tract of humans and/or animals and showing beneficial probiotic activity for the health of humans and animals. The strain *E. faecalis* GALT and/or a culture supernatant and/or metabolites thereof shows no in vitro multiresistance to antibiotics of common use in human clinics as glycopeptides, such as vancomycin, teicoplanine; carbapenemes, such as impipenem, meropenem; and ampicillin. The strain *E. faecalis* GALT contains no red blood cell-destroying hemolysins of human, ovine and equine origin; and it does not produce any gelatinase, DNase and decarboxylases.

The strain *E. faecalis* GALT is useful for the preparation of a composition intended for the treatment and/or prophylaxis of disorders associated with colonization by pathogenic microorganisms of the gastrointestinal tract; for use as a regulator of the immune response in human and animals, as well as for the preparation of a composition.

The invention is also directed to methods and uses of the strain *E. faecalis* GALT.

11 Claims, 2 Drawing Sheets

Whole cell protein profile (SDS-PAGE)

1) Prestained SDS-PAGE Standards Broad Range (BIO-RAD®)
2) *Enterococcus faecalis* ATCC 29212
3) *Enterococcus faecalis* CECT 7121

Cluster analysis of RAPD-PCR patterns generated with M13 and D8635 primers

1% agarose Gel in 0.5X TBE buffer.
Line 1: *E. faecalis* CECT 7121-1, Line 2: *E. faecalis* CECT 7121-2, Line 3: *E. faecalis* CECT 7121-3, Line 4: *E. faecalis* CECT 7121-4, Line 5: *E. faecalis* CECT 7121-5, Line 6: *E. faecalis* CECT 7121-6, Line 7: *E. faecalis* ATCC 29212 and Line 8: *E. faecalis* EVR 2000.

SEQUENCE LISTING

<160> NUMBER OF SEQ ID NOS: 2

<210> SEQ ID NO 1
<211> LENGTH: 15

```
-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagggtggcg gttct                                                        15

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagcggccaa agggagcaga c                                                 21
```

LACTIC BACTERIA USEFUL AS PROBIOTICS

The present invention is directed to a new strain of a group of lactic bacteria having probiotic activity. This strain was isolated from a natural corn silage without chemical or biological additives. Specifically, the invention provides a new strain of enterococci, *Enterococcus faecalis* GALT, capable of surviving in and colonizing the gastrointestinal tract of humans and animals, and their use as probiotics.

The present invention is also directed to compositions, uses, and methods for inhibiting the growth of pathogenic microorganisms, either in the process of manufacturing food, previous to consumption, or in uses and methods for the treatment and prophylaxis of disorders associated with the colonization of the gastrointestinal tract in humans and animals, and to uses and methods for improving the immune response (natural and acquired) in humans and animals. More specifically, the invention is related to compositions and methods for inhibiting pathogenic growth and for improving the immune response of humans and animals through the use of the inventive microorganism.

BACKGROUND OF THE INVENTION

The ingestion of pathogens, especially bacterial pathogens, including viruses and other disease-causing microorganisms, is a common problem in most animals. It is well known that pathogens cause diseases in animals, with numerous harmful effects including weight loss, diarrhea, abdominal obstruction, and renal failure. In the case of immunosuppressed or underfed animals, the effects of diarrhea may be even fatal. Pathogens are often transferred among animals under poor hygienic conditions, and even when suitable care is available, contagion may not be avoided.

Extreme health risks result when humans consume pathogens in contaminated food products such as sprouts, lettuce, meat products, unpasteurized milk or juice, water contaminated with sewage waters, etc. The problem is particularly frequent in beef and the dairy sector. Pathogens present in the udder of cows or in the milking equipment may be a source of contamination for raw milk. Beef may be contaminated in the slaughterhouse, and pathogen organisms may be subsequently mixed with large amounts of meat during grinding. Serious and life-threatening infections may occur when humans eat meat, especially ground beef, which has not been cooked enough so as to kill any pathogen present in the beef. This problem is difficult to solve because contaminated meat often looks and smells perfectly normal. Further, the number of pathogenic organisms necessary to cause a disease condition is extremely small, making detection very difficult. Pathogens that cause diseases in the intestinal zone are known as enteropathogens. Examples of these bacteria include *Staphylococcus aureus*, specific strains of *Escherichia coli* (*E. coli*), and *Salmonella* spp. While most of the hundreds of *E. coli* strains are harmless and live in the intestines of animals, including humans, some strains such as *E. coli* 0157:H7, 0111:H8, and 0104:H21, produce great amounts of powerful toxins closely related or identical to the toxin produced by *Shigella dysenterieae*. These toxins may cause severe pain in the small intestine, often producing harmful effects in the intestinal zone and in extreme cases, diarrhea. *E. coli* 0157:H7 and other enterohemorrhagic strains may also cause acute hemorrhagic diarrhea, characterized by severe abdominal obstruction and abdominal bleeding. In children, this may develop into a rare but fatal disorder called hemolytic uremic syndrome ("HUS"), characterized by renal failure and hemolytic anemia. In adults, it may develop into a condition known as thrombotic thrombocytopenic purpura ("TTP"), which involves HUS in addition to fever and neurological symptoms, and may have a mortality rate as high as of 50% in the elderly.

A reduction in the risk of diseases caused by food-borne pathogens may be achieved by controlling potential contamination sources. The beef industry has recognized the need of increasing the control of pathogens prior to harvest, particularly the control of *E. coli* 0157:H7 and other hemorrhagic serotypes, to avoid contamination of products, potential contact with humans, and transmission of pathogens during meat processing. In particular, raw or undercooked hamburgers (ground beef) have been involved in many outbursts or documented epidemics as containing *E. coli* 0157:H7 and other hemorrhagic serotypes.

Thus, there persists a recognized need for providing compositions and methods for reducing or eliminating the growth of enteropathogens such as *E. coli* 0157:H7 and other hemorrhagic serotypes, for the benefit of human and animal health.

Therefore, for the benefit of consumers, there is an important need of reducing or eliminating the growth of enteropathogens in animal meat and milk before their harvest. Such reduction or elimination of pathogens in animals intended consumption will provide a better protection for beef consumers, in dairy, and other food products against the risk of consuming said pathogens.

A very common solution to this problem has been the provision of antibiotics to the animals; however, this solution is not only costly, but may also lead to the generation or selection of antibiotic-resistant bacterial strains. Also, as is known, the treatment with antibiotics, in particular oral antibiotics, may modify or destroy the gastrointestinal flora. These antibiotics may exert a negative effect on the general health. Said negative or undesirable effect, consists in partly destroying the healthy bacteria naturally living in the body. For example, in the intestine there are healthy bacteria that usually live there: biphidobacteria and lactobacilli, that are part of the intestinal flora. Said intestinal microbiota constitute a natural defense for protection against stomach and intestine infections; infections which finally will cause problems such as diarrhea.

On numerous occasions, patients on antibiotics have diarrhea, due to destruction of the bacteria that naturally live in the intestine, and protect them against infections.

Likewise, women on antibiotics for a bacterial infection may suffer from mycosis (fungi) at vaginal level, as the antibiotics also kill the bacteria acting as natural defense (lactobacilli).

It has thus been shown that the gastrointestinal microbiota play a number of vital roles in maintaining normal function of the gastrointestinal tract and overall physiological health. For some experts, the key to good health resides in the intestine, whose role in the human body has been compared to that played by the roots of a tree. And, in fact, the intestine is not just an absorption organ. It is the most relevant site of action of the immune system and of non-specific protective mechanisms, as it is precisely in the intestines where they are most active. Its immunocompetent cells recognize pathogenic agents and activate the production of T lymphocytes that, in turn, differentiate into plasma cells and segregate non-specific antibodies.

When we are born, the gastrointestinal tract is sterile but shortly after a complex set of approximately 400 different types of microorganisms settles down permanently which work in harmony at maintaining the health. This microflora— the intestinal flora—weights over one kilogram, it may comprise up to 100 billions of different microorganisms which have an overall metabolic activity similar to that of a human liver. Once the microflora has settled, it may be negatively affected by factors such as consumption of very refined food poor in fibers, antibiotic treatments, and stress, among others.

For example, growth and metabolism of the many individual bacterial species living in the gastrointestinal tract depend mostly on the available substrates, mainly derived from the diet. See, for example. Gibson et al., 1995. *Gastroenterology* 106: 975-982; Christi, et al., 1992. *Gut* 33: 1234-1238; Gorbach, 1990. *Ana. Med.* 22: 37-41; Reid et al, 1990. *Clin. Microbiol. Rev.* 3: 335-344. These disclosures have led to different approaches intended to modify the structure and metabolic activity of the gastrointestinal tract through the diet, especially including probiotics, which are live microbial food supplements.

As it is known that pathogens live in many different areas of the digestive system of animals, it has been found beneficial to supply and/or reinforce the naturally-occurring organisms in these areas which are effective for inhibiting pathogenic growth throughout the digestive tract, such as in the rumen, small intestine, and large intestine.

Probiotics, when introduced into the gastrointestinal tract, may influence the gastrointestinal microflora and play a beneficial role in the human or animal host. The term "probiotic" derives from Greek "for life". It was first used to describe substances secreted by microorganisms capable of stimulating the growth of other microorganisms (Lilly and Stillwell, 1965, Probiotics: growth-promoting factors produced by microorganisms. *Science*. February 12; 147:747-8).

In 1992, Havenaar suggested, as a definition for probiotics, "a viable mono- or mixed culture of microorganisms, which applied to animals or man, beneficially affects the host animal by improving the properties of the indigenous microflora" (Havenaar et al., 1992, Selection of strains for probiotic use. In: *Probiotics, the Scientific Basis* (Fuller R., ed.), pp. 209-224. Chapman and Hall, London, UK). Havenaar's definition was the first using the term probiotic for both humans and animals.

Taking into account the current applications and proven effects of probiotics, Salminen et al (1999), Probiotics: how should they be defined. *Trends Food Sci. Tech.;* 10:107-110), proposed a new definition: "probiotics" are preparations of microbial cells or components of microbial cells that exert a beneficial effect on health and comfort of the host. This definition includes microbial cells (viable or non-viable) and parts of cells as probiotics, but not metabolites such as antibiotics. This definition also indicates that the application of probiotics is not restricted to its use in food.

"Probiotics" are considered as viable microbial preparations that promote the health of an individual by preserving a healthier microflora in the intestine. A microbial preparation is commonly accepted as a probiotic when it as a known effect and mode of action. Probiotics bind to the intestinal mucosa, colonize the intestinal zone and also prevent settling of deleterious microorganisms into the intestine. An essential requirement for its action is that they should reach the intestinal mucosa in an appropriate and viable way without being destroyed at the upper part of the gastrointestinal tract, especially by influence of the low pH values prevailing in the stomach.

It is known that the low pH values in the stomach in addition to the antimicrobial action of pepsin provide an efficient barrier against the entry of bacteria into the intestinal zone. The pH of the stomach ranges from 2.5 to 3.5, but may reach values as low as pH 1.5, or as high as pH 6 or higher after food ingestion. The type of food affects stomach emptying. Normally, food remains in the stomach from two to four hours: however, liquids leave the stomach in about 20 minutes. Extensive in vitro tests have been used for selecting gastric tolerance, including lactic acid producing bacteria tolerant to acids (Charteris et al, 1998, Development and application of an in vitro methodology to determine the transit tolerance of potentially probiotic *Lactobacillus* and *Bifidobacterium* species in the upper human gastrointestinal tract. *J. Appl. Microbiol.* May; 84(5):759-68; Clark et al, 1993, Selection of bifidobacteria for use as dietary adjuncts in cultured dairy foods: III. *Cult. Dairy Prod. J.* 29:18-21; Chou and Weimer, 1999, Isolation and characterization of acid- and bile-tolerant isolates from strains of *Lactobacillus acidophilus. J Dairy Sci.* January; 82(1):23-31).

Another barrier that probiotic bacteria must overcome is the small intestine. The adverse conditions of the small intestine include the presence of bile salts and pancreatin. The transit time of food through the small intestine generally comprises between one and four hours. Lactic acid bacteria resistant to bile salts may be selected by assaying their survival capacity in the presence of bile salts and their growth on selective media with varying levels of bile (Gilliland et al, 1984, Importance of bile tolerance of *Lactobacillus acidophilus* used as a dietary adjunct. *J Dairy Sci.* December; 67(12):3045-51; Ibrahimand Bezkorovainy, 1993, Survival of bifidobacteria in the presence of bile salt. *J Animal Sci.* 62:351-354; Clark and Martin, 1994, Selection of bifidobacteria for use as dietary adjuncts in cultured dairy foods: II—tolerance to simulated pH of humans stomach. *Cult. Dairy Prod. J.* 6:11-14; Chung et al, 1999, Screening and selection of acid and bile resistant bifidobacteria. *Int. J. Food Microbiol.* 47:25-32). A concentration of 0.15-0.3% of bile salts is a suitable concentration for selecting probiotics for human use.

After surviving the passage through the upper gastrointestinal tract, probiotic bacteria need to attach to the intestinal epithelium in order to colonize and remain in the gastrointestinal tract. The complexity of the intestinal mucosa and its microflora make it very difficult to study bacterial attachment in vivo.

Live probiotic microorganisms may provide advantages either during the preparation of fermented probiotic food or in the digestive tract of the host. After fermentation, texture and flavor of the raw materials are perceptibly improved; harmful effects of some feed components may be reduced, for example food intolerance and allergies caused by certain oligosaccharides and proteins; levels of amino acids and vitamins may be improved, which enhances the nutritional value of food; and sugars and other components that promote food decay may be removed, leading to a longer potlife and improving the safety of food products. Also, there is evidence that the bioavailability of calcium, zinc, iron, manganese, copper, and phosphorus is greater in fermented yoghurt as compared to milk. Studies have also showed an increase in riboflavin and niacin in yoghurt, vitamin B6 Cheddar cheese, vitamin B12 in quark and folic acid in a variety of products including yoghurt, quark, Cheddar cheese, and sour cream. Enzymatic hydrolysis of probiotic microorganisms has also demonstrated to enhance bioavailability of proteins and fats. Bacterial protease may increase the production free amino acids that may benefit the nutritional condition of the host, especially if said host has an endogenous protease deficiency.

In the food manufacturing industry, the lactic bacteria used as protecting cultures must have the ability to adapt themselves to the prevailing conditions in the corresponding product and must also show competitive ability. In most beef products, lactic bacteria must tolerate relatively high salt concentrations, and should be able to develop in the presence of nitrite at relatively low temperatures. Biological preservation of food is an important alternative to preservation with non-biodegradable chemical compounds which are toxic for humans.

It has also been disclosed that consumption of food containing viable probiotics produces health benefits including (1) alleviation of intestinal disorders such as constipation and diarrhea caused by an infection by pathogenic organisms, antibiotics, or chemotherapy; (2) stimulation and modulation of the immune system; (3) anti-tumoral effects resulting from inactivation or inhibition of carcinogenic compounds present in the gastrointestinal tract by reduction of intestinal bacterial enzymatic activities such as O-glucuronidase, azoreductase, and nitroreductase; (4) reduced production of toxic final products such as ammonia, phenols and other protein metabolites known to influence hepatic cirrhosis (5) reduction of serum cholesterol and arterial pressure; (6) maintenance of mucosal integrity; (7) alleviation of lactose intolerance symptoms; (8) prevention of vaginitis.

Examples of probiotic organisms include, but are not limited to, bacteria capable of growing, at least temporarily, inside the gastrointestinal tract, of displacing or of destroying pathogenic organisms, as well as providing additional advantages to the host.

It is known that certain bacteria, in particular bacteria isolated from healthy human or animal gastrointestinal tracts, as well as certain lactic acid bacteria such as *Lactobacillus*, have a prophylactic and therapeutic effect in gastrointestinal diseases, such as gastrointestinal infections. For this purpose, the administration of preparations containing these microorganisms (viable) to humans or animals is also known. After administration, these probiotic bacteria (also called eubiotic) compete with the pathogenic bacteria for food and/or binding sites on the gastrointestinal wall, such that their number is reduced and infections are thus reduced or prevented.

For many years, lactic acid bacteria have been used as fermenting agents for food preservation by reason of their low pH and the action of the fermentation products generated during their fermentation activity which inhibits the growth of harmful bacteria. To this end, lactic acid bacteria not well characterized yet have been used for preparing a variety of food products such as dry fermented meat products, cheese, and other fermented dairy products.

Recently, these lactic acid bacteria have attracted some attention because it has been found that some strains exhibit valuable characteristics for digestion in humans and animals. In particular, specific strains of the genera *Lactobacillus* or *Biphidobacterium* capable of colonizing the intestinal mucosa and assisting in the maintenance of wellbeing of humans and animals were found.

The best-known probiotics are lactic-acid generating bacteria (that is, lactobacilli and biphidobacteria), extensively used in yoghurts and in other milk products. These probiotic organisms are non-pathogenic and non-toxic, they maintain viability during storage, and survive the passage through the stomach and the small intestine. As the colonization of the host by probiotics is not permanent, they must be consumed on a regular basis in order to achieve persistent health-promoting characteristics. Commercial probiotic preparations generally comprise mixtures of lactobacilli and biphidobacteria, but species of yeast such as *Saccharomyces* have also been used.

In this aspect, several patent applications disclose specific strains of Biphidobacterium, *Lactobacillus* and, to a lesser extent, *Enterococcus* (*E. faecium*) and their beneficial effects on diarrhea, immuno-modulation, hypersensitive reactions or infections by pathogenic microorganisms.

In spite of the above-mentioned beneficial effects of these probiotics, as the bacteria that may be administered for treating gastrointestinal disorders also have preferred adhesion and/or growing sites in the gastrointestinal tract, and these sites may be different from the growing sites of the deleterious microorganisms to be controlled, administration of certain types of probiotic bacteria may not be of help against certain types of gastrointestinal infections.

Thus, *Lactobacillus, Lactococcus*, or *Micrococcus* may be located in the mouth, and preferably in the small intestine extending even to the ileum. Accordingly, administration of these bacterial genera will not be of great use against infections by pathogenic microorganisms, such as *E. coli, Salmonella, Clostridium, Shigella*, and *Campylobacter*, because they develop in other parts of the gastrointestinal tract, such as the colon.

On the other hand, biphidobacteria and enterococci grow in the anaerobic part of the gastrointestinal tract. Biphidobacteria are preferably located in the colon. Species of *Enterococcus* are preferably located in ileum and colon.

Another difficulty observed with many strains of enterococci useful as probiotics (for example, *E. faecium*), is that they show a natural resistance to the antibiotics of clinical use in man. Currently, the trend is not to incorporate bacteria with multiple resistance to antibiotics as additives of food products. There is a possibility of transferring said resistance to saprophytic bacteria colonizing the intestine. In addition, due to a condition of immunosupression (AIDS; chemotherapy in cancer, congenital immunologic dyscrasia, etc) or to an abdominal trauma, this antibiotic resistant probiotic bacteria that colonized the intestine may advance to the peritoneum or to the blood and originate infections difficult to treat due to their multi-resistance.

Accordingly, there persists a need for providing a therapeutic method as an alternative to prescription of highly efficient antibiotics and which would work in acute, as well as preventive, treatment scenarios with inhibitory activity against pathogenic bacteria, including those that are resistant to those antibiotics currently used for infections in humans and animals. In addition, the new agent should have inhibitory activity against other pathogenic organisms such as parasites and fungi.

There is also a need for this therapeutic method to be efficient against infections by pathogenic microorganisms not localized in those parts of the gastrointestinal tract where Biphidobacterium and *Lactobacillus* are localized, and that it also capable of being administered in combination with antibiotics.

An additional need is to provide a new probiotic strain which is not resistant to antibiotics of clinical use such as glycopeptides (vancomicin, teicoplanine), carbapenemes (impipenem, meropenem) and ampicillin and with a broad inhibitory spectrum against Gram positive and Gram negative bacteria, as well as against other parasitic, fungal and viral pathogens.

DEPOSIT INFORMATION

Figure 1:
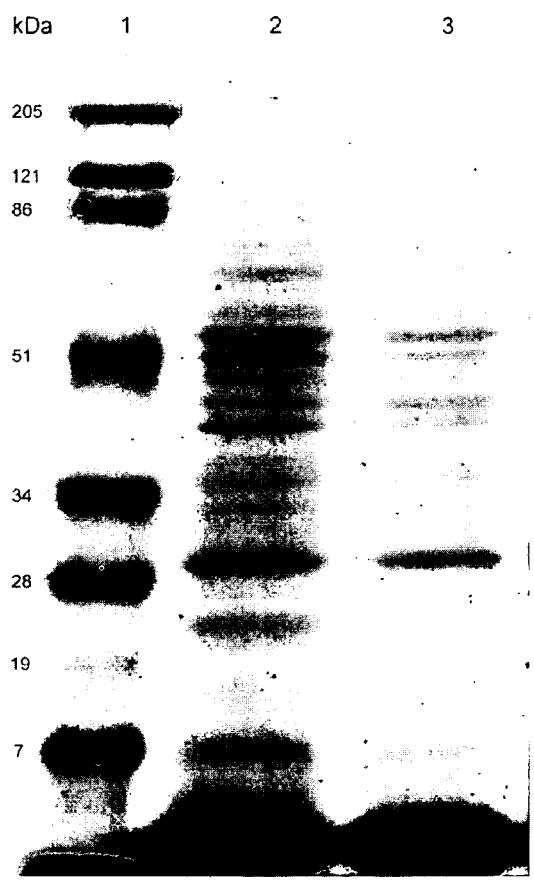
FIG. 1 shows the profile of cell proteins described in Example I.

An isolated strain of *Enterococcus faecalis* GALT was deposited in The Spanish Collection of Type Cultures, 46100 Burjassot (Valencia). Spain, as *E. faecalis* CECT7121, on Dec. 1, 2005

SUMMARY OF THE INVENTION

The present invention is directed to a new strain from the group of lactic bacteria, capable of surviving and colonizing the gastrointestinal tract in humans and/or animals and having a probiotic activity which is beneficial for the health of humans and animals.

Particularly, the invention provides a new strain of enterococci, *E. faecalis* GALT isolated from a natural corn silage without chemical or biological additives, useful as a probiotic.

Therefore, according to a first aspect of the invention, a new probiotic strain belonging to the group of lactic bacteria, preferably of the genus *Enterococcus*, is provided. This strain was selected for its ability to survive and colonize the gastrointestinal tract of humans and/or animals, and to exert a beneficial probiotic activity for the health of humans and/or animals.

In another aspect, the invention provides a new probiotic strain from the group of lactic bacteria, preferably a strain of *Enterococcus*, which is not resistant in vitro to antibiotics of clinical use for this genus.

This selected microorganism has a particular beneficial impact on humans and/or animals, both on their gastrointestinal tract and/or their immune system. It has a particular impact on intestinal pathogens such as strains of *Salmonella typhimurium*, of *Escherichia coli* enteropathogens, of *Shigella dysenterieae*, and other pathogenic enterobacteria capable of infecting man, or parasites such as helminthes (*Toxocara canis*), protozoa (*Cryptosporidium* spp, *Giardia lambia, Entamoeba histolytica, Toxoplasma gondii, Dientamoeba fragilis*) or yeasts (*Candida* spp.).

Therefore, a further aspect of the invention is directed to the use of the bacterial strain *E. faecalis* GALT and/or of its culture supernatant and/or of its metabolites for the preparation of a composition intended for the treatment and/or prophylaxis of disorders associated with colonization of the gastrointestinal tract by pathogenic microorganisms.

Unless the context clearly indicates otherwise, reference to "strain" is meant to include the strain itself, as well as the culture supernatant and/or a metabolite thereof.

Thus, in another aspect, the invention refers to the use of the bacterial strain *E. faecalis* GALT and/or a culture supernatant thereof and/or a metabolite thereof, for preparing a composition intended for use as a regulator of the immune response in humans and animals.

By the term "regulator of the immune response" is meant a bacterial strain as defined herein and/or a culture supernatant thereof and/or its metabolites capable of stimulating certain immune functions which are important for the health of humans and/or animals, or to modulate other immune functions that could potentially be involved in immune disorders, such as inflammation, allergy, etc.

The microorganism of the invention shows bioprotective activity with fermented and non-fermented plant, milk and meat food products.

Thus, according to another aspect, the invention is directed to the use of the isolated strain *E. faecalis* GALT and/or a culture supernatant thereof and/or a metabolite thereof, for food preservation, comprising adding a sufficient amount of the isolated strain *E. faecalis* GALT to the food product to be efficient as a bioprotector.

The invention also provides a method for maintaining or improving the health of the gastrointestinal tract, or of the immune system of humans and/or animals comprising the step of administering to said subject a composition containing the isolated strain *E. faecalis* GALT.

Further, the invention provides a method for the treatment and/or prophylaxis of disorders associated with colonization of the gastrointestinal tract of humans and/or animals by pathogenic microorganisms, comprising the step of administering to said man or animal a food or feed composition containing the isolated strain *E. faecalis* GALT.

The invention also provides a method for regulating the immune response in humans and/or animals, comprising the step of administering to a man and/or animal a composition containing at least the isolated strain *E. faecalis* GALT according to the present invention.

According to still another aspect, the invention is related to a method for preserving food consisting in adding a sufficient amount of the isolated strain *E. faecalis* GALT and/or a culture supernatant thereof and/or a metabolite thereof as a bioprotector.

Combined with food, the beneficial probiotic effects of this microorganism consist particularly in a pleasant flavor, a healthy digestion and intestines, and improvements in the immune function.

Thus, according to still another aspect, the invention is related to a food composition comprising the strain *E. faecalis* GALT having high probiotic activity in humans and/or animals and capable of surviving and colonizing the gastrointestinal tract of humans and/or animals ingesting it.

Accordingly, the invention is related to a food composition intended for the treatment and/or prophylaxis of disorders associated with colonization of the gastrointestinal tract of humans and/or animals, containing the isolated probiotic strain *E. faecalis* GALT and/or a culture supernatant thereof and/or a metabolite thereof, associated with an edible carrier or a pharmaceutical matrix.

Also, the invention is related to a food composition intended for regulating the immune response in humans and/or animals, containing the isolated strain *E. faecalis* GALT and/or a culture supernatant thereof and/or a metabolite thereof, associated with an edible carrier or a pharmaceutical matrix.

In a further aspect, the invention provides a bioprotective food composition containing the isolated probiotic strain *E. faecalis* GALT and/or a culture supernatant thereof and/or a metabolite thereof, associated with an edible carrier or a pharmaceutical matrix.

The food composition preferably contains a sufficient amount of the isolated strain, *E. faecalis* GALT and/or a culture supernatant thereof and/or a metabolite thereof, to be efficient at providing said prophylactic effect when the composition is administered to a human or animal.

DETAILED DESCRIPTION OF THE INVENTION

The presence in corn silage of lactic bacteria capable of surviving and colonizing the gastrointestinal tract of humans and/or animals, and of providing a beneficial probiotic activity for the health of a human or an animal, was investigated. These bacterial strains show good adhesion to the mucosal cells of the small intestine.

Three strains of *Lactobacillus* and four strains of *Enterococcus faecalis* were screened for "bacteriocine" type compounds. The strain of *E. faecalis* designated GALT was further investigated.

The strain of the invention does not have hemolysins that destroy red blood cells of human (4 blood types), sheep and horse origin. It does not produce gelatinase, Dnase, and decarboxylases (Example 1 (a)-(b)).

The strain *E. faecalis* GALT of the invention produces a protein-type antimicrobial substance (broad spectrum inhibitory bacteriocine). The inhibitory component, partially purified enterocine designated EPP, was obtained by precipitation with ammonium sulphate, and after elution with Sep-Pak 018. EPP it was heat-inactivated during 15 min at 121° C. or by treatment with 2-mercaptoethanol as well as with Triton X-100. EPP is partially hydrophobic and further maintains its activity in the range of pH 4-8. EPP has a molecular mass of 5,000 Da.

EPP showed bactericidal action on *L. monocytogenes, S. aureus*, Gram positive strains resistant to antibiotics of clinical use and bovine-mastitis producing strains. Further, EPP showed bacteriostatic action on different strains of *E. coli*.

When analyzed by RP-HPLC cromatography, EPP shows inhibitory activity in the sample eluted with 40% acetonitrile. The strain *E. faecalis* GALT of the invention is a saprophytic environment lactic bacterium, without virulence factors; i.e. it does not produce proteases and hemolysines, it does not show antibiotic multiresistance, and has in vitro inhibitory activity against numerous strains of Gram positive bacteria such as *Listeria monocytogenes, Staphylococcus aureus, Streptococcus pneumoniae, Enterococcus faecalis (E. faecalis* GALT shows immunity to its inhibitory activity), *E. faecium, E. durans, E. gallinarum-casseliflavus, Str. agalactiae, Str. dysgalactiae, Str. uberis, Clostridium perfringens, C. sporogenes, Bacillus subtilis,* and *B. cereus.* It also acts against some Gram negative bacteria such as certain strains of *E. coli, Shigella sonnei,* and *Shigella fexneri.* However, the lactic acid bacteria used as starters in fermented food such as certain strains of *Lactobacillus, Leuconostoc,* and *Pediococcus* are resistant to the action of *E. faecalis* GALT strain (Example II).

Further, it shows inhibitory action against Gram-positive strains with multi-resistance to antibiotics and also against the most important agents of bovine mastitis and endometritis in mares.

In this way, the strain of the invention may form a protecting barrier against pathogenic bacteria such as the different types of intestinal pathogens of *Escherichia coli, Salmonella* spp, *Staphylococcus aureus, Candida* spp, as well as against parasitic infections by *Toxocara canis, Giardia lambia, Entamoeba* spp, *Cryptosporidium.* spp.

The strain of the invention is also characterized in that it does not show multi-resistance in vitro to commonly used antibiotics in human clinics such as ampicillin, vancomycin, teicoplanine, tetracycline, and chloramphenicol. It has not a high level of resistance to gentamycin (120 μg) and streptomycin (300 μg) (Example 1 (c)).

The strain *E. faecalis* GALT of the invention may be used in any therapy either for preventing colonization by harmful organisms; or for reestablishing gastrointestinal flora after antibiotic treatment. When *E. faecalis* GALT is ingested at a high concentration by humans and/or animals, this bacterium colonizes the intestine creating the necessary environment for a useful and homogeneous flora. Administration of *E. faecalis* GALT to said human and/or animal may also act against the deleterious effects of antibiotics, as well as complete the recovery of humans and animals, avoiding recycling of intestinal bacteria in the case of diarrheas. On the other hand, it prevents contagion of pulmonary diseases in weak humans and animals, for example those recently weaned or separated from their mother (pig breeding)

An early investigation on the potential uses of probiotics was carried out in vitro and consisted in the study of tolerance to gastric acidity with various pH values (Example 1 (d)) and different concentrations of bile salts encountered in the duodenum (Example 1 (e)). Assays show that *E. faecalis* GALT is able to survive the acid environment of the stomach, and the presence of bile salts and the digestive process.

The strain *E. faecalis* GALT according to the invention colonizes raw food of different animal origin and resists adverse environmental conditions (heat, pH acids, high NaCl concentrations) and may survive in fermented products. (Examples 2-4). In this way, it plays an important role in the natural preservation of meat products by controlling the development of various pathogenic or harmful bacteria (coliforms, staphylococci). The strain tolerates the relatively high salt concentrations of meat products and develops in the presence of nitrite and relatively low temperatures, showing a great resistance to technological processes.

Biological preservation of food is an important alternative to preservation with non-biodegradable chemical compounds, which may be toxic to humans. In this way, the strain of the invention may be included in food products as a biological preservative, thus avoiding the use of non-biodegradable chemical preservatives that are toxic to humans.

Also, the strain according to the invention may be incorporated into food products, thus forming a new kind of functional food product, as it is an enriched food providing not only nutritional benefits to those ingesting it but also other advantages allowing for better health conditions. *E. faecalis* GALT according to the invention colonizes the intestine thereby positively modifying the intestinal flora and improving the immune system function and, accordingly, the general health of the organism.

The strain *E. faecalis* GALT of the invention acts not only on innate immunity, as other probiotic strains, but also on specific or acquired immunity. *E. faecalis* GALT activates peritoneal macrophages in culture and induces production of both IL-12 and IL-10. *E. faecalis* GALT can also establish a good balance between anti-inflammatory cytokine IL-10 and pro-anti-inflammatory IL-12 (either suppressing inflammatory responses or enhancing them) in order to maintain such an important function as immune homeostasis in the host. When *E. faecalis* GALT is pre-administered intragastrically in immunized mice with bacterial vaccines (Diphtheria-Tetanus-Pertussis), it produces an increase of the proliferative response memory of specific T lymphocytes thus stimulating the production of type Th1 (INF-γ) and Th2 (IL-5).

The invention will be described with more detail by reference to the following examples of different embodiments, but the invention is in no way to be considered as limited to any specific embodiments.

EXAMPLE I

Biochemical Characterization of *Enterococcus faecalis* GALT a) Hemolytic Activity The study of hemolytic activity of *E. faecalis* GALT was carried out using human (all four blood types), ram and horse red blood cells. A *E. faecalis* GALT culture of 18 h in brain-heart infusion was used for isolations on base agar Columbia supplemented with blood of different origin (5%, v/v), Plaques were incubated under anaerobic conditions (Gas-Pack system) at 35° C., and monitored for 24 h and 72 h after incubation. Surrounding the colonies, the presence of a clear zone of hydrolysis (β hemolysis), partial action (α hemolysis) or absence of hemolytic activity (γ hemolysis) were analyzed. The strain *E. faecalis* GALT did not hydrolyze red blood cells of different origin (γ hemolysis) which is why there is no production of hemolysins.

b) Production of Gelatinase

The production of gelatinase by *E. faecalis* GALT was determined by addition of mercurial chloride to a culture on agar with gelatin. The study of the production of thermonucleases, such as DNAse, was carried out according to Giraffa et al. (1995) from a culture of *E. faecalis* GALT in Todd Hewitt broth with 1% yeast extract and boiled broth (boiled broth culture). Decarboxylases were evaluated according to the method of Joosten and Northolt (1989), Detection, growth, and amine-producing capacity of lactobacilli in cheese. *Appl. Environ. Microbiol.* 55, 2356-2359, modified by Maijala (1993), Formation of histamine and tyramine by some lactic acid bacteria in MRS-broth and modified decarboxylation agar. *Letters in Applied Microbiology* 17, 40-43. The following amino acids were used: ornithine, histidine, tryptophan, lysine, phenylalanine, and tyrosine. Gelatinase, DNase, decarboxylases were not detected in the strain *E. faecalis* GALT according to the invention.

c) Resistance to Antibiotics

The study of resistance of *E. faecalis* GALT to antibiotics was carried out using the diffusion through agar technique with monodiscs (Lab. Britania): ampicillin (10 μg), gentamicin (120 μg), streptomycin (300 μg), erythromycin (15 μg), vancomycin (30 μg), teicoplanine (30 μg), tetracycline (30 μg), chloramphenicol (30 μg), using Mueller-Hinton agar as culture medium (NCCLS, 2004). The production of the beta-lactamase enzyme (Nitrocefin) was also investigated. *E. faecalis* GALT does not show resistance in vitro to the above-mentioned antibiotics, except for erythromycin. The strain *E. faecalis* GALT according to the invention does not produce beta-lactamasa enzyme.

d) Resistance to Human Fluids—Gastric Acidity

The survival of *E. faecalis* GALT at pH 2.5 was measured in the study of tolerance to gastric pH. *E. faecalis* GALT cultures in brain-heart infusion at pH 7.3 and at pH 2.5 (approximate count at $10^7$ UFC/ml) were used.

In the course of incubation during 8 h at 35° C., the value of optic density (A620) was measured and at 1 h intervals, and the population of viable bacteria was evaluated at pH 2.5 using brain-heart agar (24 h at 35° C.). It was determined that the viable population of *E. faecalis* GALT decreased to a value of 6.53 log UFC/ml after 7 h of incubation when the pH of the culture was of 2.5.

Experiments were carried out twice in duplicate.

The assays show that *E. faecalis* GALT is capable of surviving the acid environment of the stomach, in the presence of bile salts and the digestive process, and is capable of colonizing the intestine.

e) Resistance to Human Fluids—Bile Salts 0.1 ml of a culture of the strain *E. faecalis* GALT was inoculated after 18 hours in brain-heart infusion into a medium with agar, bile (40%) and esculin; growth and attack on esculin were observed after 18 h of incubation under normal atmosphere at 35° C.

The strain *E. faecalis* GALT of the invention grew rapidly and was darkened by esculin. Therefore, the strain *E. faecalis* GALT of the invention shows tolerance to bile (40%).

f) Whole Cell Protein Profile

As an additional phenotypical characterization, a whole cell protein SDS-PAGE profile (WCP) was carried out (Merquior et al., 1994). The relationship between the profiles corresponding to *E. faecalis* CECT7121 and *E. faecalis* ATCC 29212 (reference strain) was studied by densitometric analysis employing Image Pro and Origin 6.0 software (Germany). Homology percentage values were calculated using Dice's coefficient (Dice, 1945). *E. faecalis* CECT7121 presented a protein profile with aprox. a 78.5% homology with the *E. faecalis* ATCC29212 strain (FIG. 1). The whole protein cell profiling study confirmed the strain E, faecalis CECT7121 at the species level and showed its characteristic WCP.

FIG. 1 shows the profile of cell proteins (SDS-PAGE)

g) Polymerase Chain Reaction Using Random Amplified Polymorphic DNA (RAPD-PCR)

RAPD-PCR (polymerase chain reaction using random amplified polymorphic DNA) patterns proved to be useful for species identification and for the detection of inter-strain variations.

The chromosomic DNA profile was analyzed from isolates of different culture media of strain *E. faecalis* CECT7121 by RAPD-PCR and compared to other strains of *Enterococcus* of clinic origin (*E. faecalis* EVR2000) and collection (*E. faecalis* ATCC 29212) grown in brain heart infusion.

DNA was extracted according to the method of Persing et al. (1993), Diagnostic Molecular Biology, Principles and Application. Washington D.C.: ASM. The random primers used for DNA amplification in concordance with Suzzi et al. (2001), A survey of the enterococci isolated from an artisanal Italian goat's cheese (semicotto caprino) J. Appl. Microbial., 89, 267-274, were:

```
1- M13:    5' GAGGGTGGCGGTTCT 3' (SEQ ID NO: 1)

2- D8635:  5' GAGCGGCCAAAGGGAGCAGAC 3' (SEQ ID NO:
              2)
```

Amplification, electrophoresis, pattern recognition, and normalization were performed as described previously by Suzzi et al. (2001). For each strain, the normalized profiles obtained with the four different primers were assembled one after the other into a combined profile using Gel Compar version 4.1 software. These combined patterns were imported into the Bionumerics version 1.5 software (Applied Maths) and were analyzed by using the Pearson product moment correlation coefficient and the unweighted pair group with mathematical average clustering algorithm (UPGMA).

Culture Media Used with *E. faecalis* CECT7121

1—brain heart infusion (Lab. Britania, Argentina)
2—triptic soy broth (Lab. Britania, Argentina)
3—skim milk 10% (p/v) (Difco, USA)
4—M17 broth (Difco, USA)
5—MRS broth (Lab. Britania, Argentina)
6—Mueller Hinton broth (Lab. Britania, Argentina)

The results obtained were:

RAPD-PCR D8635:

2. Isolates of *E. faecalis* CECT7121 strains from different isolation media showed identical profiles.

3. Non-related isolates *E. faecalis* ATCC 29212 and *E. faecalis* EVR 2000 were detected, having a similarity percent of less than 60%.

RAPD-PCR M13:

The results obtained by this method were redundant to those obtained by RAPD-PCR D8635.

With the methods employed it was possible to discriminate non-related isolates with a low percentage of similitude, and to pool all the isolates of *E. faecalis* CECT7121 from different isolation media having an identical profile with a similarity percent of 100% (taking both methods into account).

Figure 2:
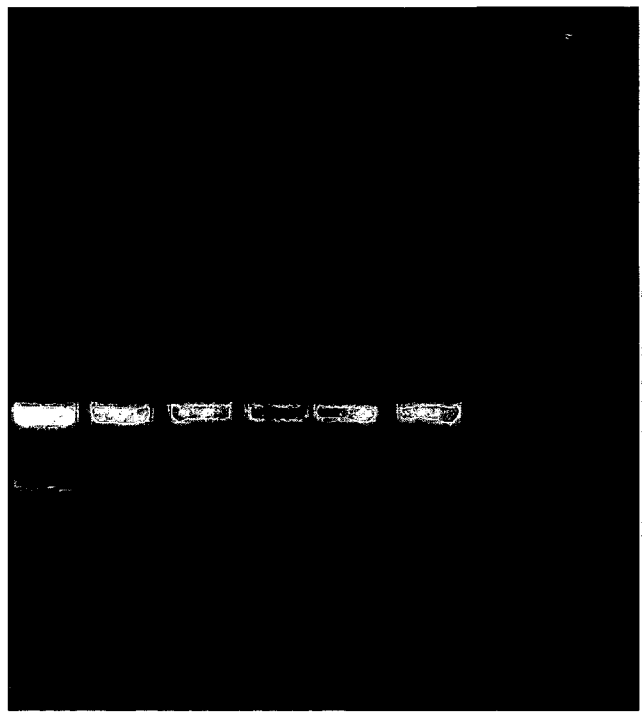
FIG. 2 shows the cluster analysis of RAPD-PCR patterns generated with M13 and D8635 primers, as described in Example I.

FIG. 2. shows the cluster analysis of RAPD-PCR patterns generated with M13 and D8635 primers

EXAMPLE II

In Vitro Antibacterial Activity of *E. faecalis* GALT

Screening for inhibitory activity was carried out using a modified version of the "double layer technique" (Tagg et al., 1975, Bacteriocins of Gram-positive bacteria. *Bacteriol. Rev.* 40, 722-756). *E. faecalis* GALT cultures were assayed after 18 h incubation in brain-heart infusion. Plates with brain-heart, previously inoculated with 5 μl of material, were incubated under anaerobic conditions (24 h at 30° C.). Then, each plate was covered with 7 ml soft agar (7 g/L) inoculated with 0.1 ml of the indicator strain (about $10^7$ UFC/ml). Plates were incubated during 18 h, under aerobic or anaerobic conditions, according to the requirements of the indicator strain.

The strain *E. faecalis* GALT showed in vitro inhibitory activity against Gram-positive bacteria: *Listeria monocytogenes*, *Staphylococcus aureus*, *Streptococcus pneumoniae*, *E. faecium*, *E. durans*, *E. gallinarum-casseliflavus*, *Str. agalactiae*, *Str. dysgalactiae*, *Str. uberis*, *Clostridium perfringens*, *C. sporogenes*, *Bacillus subtilis*, and *B. cereus*. It also showed activity against some Gram-negative bacteria, such as certain strains of *E. coli*, *Shigella sonnei*, and *Shigella fexneri*. However, the lactic acid bacteria used as starters in fermented food, such as certain strains of *Lactobacillus*, *Leuconostoc*, and *Pediococcus*, are resistant to the action of *E. faecalis* GALT.

EXAMPLE III

Bactericidal Effect of *E. faecalis* GALT on *L. monocytogenes* in Goat Milk In order to analyze the effect of this strain on deteriorating or pathogenic bacteria present in milk, the inhibitory activity on the pathogen *L. monocytogenes* resistant to environmental conditions was used as a model.

The inhibitory ability of *E. faecalis* GALT was investigated when competing with autochthonous bacteria of goat milk, against *L. monocytogenes* CEB 101 and *L. monocytogenes* ATCC 49594 (derived from the strain Scott A, which in studies carried out by other authors in milk and cheese, showed higher resistance to the inhibitory action of enterocin-producing strains). The system employed in the research excluded the influence of other inhibitory factors such as very acid pH and hydrogen peroxide.

For the production of the inhibitory component, a culture incubated 18 h at 35° C. of *E. faecalis* GALT in brain-heart infusion was centrifuged at 10,000×g during 10 min and suspended in an equal volume of PBS. Raw goat milk was skimmed at 35° C. by centrifugation in aliquots of 250 ml which were inoculated with 1% and 2% (v/v) of a suspension of *E. faecalis* GALT. In order to allow for the competition between autochthonous bacteria of milk and the inoculated strain, mixtures were incubated at 30° C. during 9 h.

For the inhibition studies of *L. monocytogenes*, the different aliquots of goat milk inoculated with *E. faecalis* GALT (1% and 2%), were acidified to a pH of 4.2 with 1N HCl to curdle the caseins, and centrifuged at 20,000×g during 15 min. Each supernatant was filtered with a 0.22 μm diameter membrane (Millipore) and pH was adjusted at 6.0 with 1N NaOH. Fractions of 10 ml of this filtrate were obtained and inoculated with *L. monocytogenes* CEB 101 and ATCC 49594 to obtain a final count of viables of about $10^4$ UFC/ml. Catalase (150 UI/flip was added to the inoculated filtrates and they were incubated during 24 h at 30° C.

Then, the two strains of *L. monocytogenes* were isolated and enumerated from selective Oxford agar (Oxoid), at 30° C. during 48 h.

Inhibition studies were also carried out with 10 strains of wild-type *L. monocytogenes* isolated over the last five years from raw goat milk (GM) obtained from different farms where home-made semihard cheese is manufactured (Buenos Aires Province).

Each strain was inoculated in 10 ml of 2% *E. faecalis* GALT filtrate, previously incubated during 9 h at 30° C. After 24 h of incubation with the filtrate, each strain was measured.

Also, the inhibition test in the strains of wild-type *L. monocytogenes* was carried out with the 2% *E. faecalis* GALT filtrate and using the well diffusion technique.

All the strains of *Listeria* came from a culture grown to logarithmic phase, in brain-heart infusion incubated at 30° C. All experiments were repeated 3 times, in duplicate, and the results were statistically analyzed using Student's t test.

When the inhibitory effect of the filtrate against *Listeria monocytogenes* ATCC 49594 and CEB 101 was analyzed, the decrease of viable counts observed in *L. monocytogenes* ATCC 49594 and CEB101 was significantly and directly influenced ($p<0.001$) by the inoculum of 2% *E. faecalis* GALT strain, wherein the decrease of viables in both strains of *Listeria* was greater than 2.5 log UFC/ml and in *L. monocytogenes* CEB101, 3.25 log UFC/ml.

The 10 wild-type strains recovered from different farming facilities were sensitive to the action of the *E. faecalis* GALT filtrate when inoculated at 2% and previously incubated during 9 h at 30° C.; diameters of inhibition obtained by the well diffusion technique varied from 11.3 and 12.9 mm.

Count variations were significant for all strains when incubated during 24 h ($p<0.01$).

The decrease of the viable population was greater than 1.8 log UFC/ml for all wild-type strains under study.

Inoculation of raw goat milk with a 2% suspension of *E. faecalis* GALT could control the growth of diverse strains of *L. monocytogenes* recovered from raw milk intended for use as starting material for home-made cheese.

The strain *E. faecalis* GALT competed with the native microorganisms from goat milk, that was a favorable substrate for the production of inhibitory activity.

In these experiments, inhibitory factors, such as lactic acid, acid pH, and hydrogen peroxide, were eliminated by neutralizing the milk cultures and by the use of catalase.

The strain *E. faecalis* GALT was able to compete with the native microorganisms from goat and cow milk and showed bactericide activity against *L. monocytogenes*, a contaminating pathogen resistant to environmental conditions present in goat and cow milk. The system excluded the influence of other inhibitory factors such as very acid pH, lactic acid and hydrogen peroxide.

EXAMPLE IV

Inhibitory Activity of *E. faecalis* GALT Against Bacterial Flora of Ready-To-Eat Vegetables The effect of the addition of *E. faecalis* GALT on the growth dynamics of bacteria associated to ready-to-eat vegetables was analyzed during storage at 8° C.

A 9 h culture of *E. faecalis* GALT in brain-heart infusion was centrifuged during 10 min at 10000×g. It was washed and suspended in Ringer solution and added to 3 different mixtures of vegetables so as to obtain a final count of about 106 UFC/g. For each salad variety a control group was established using Ringer solution.

The trays containing ready-to-eat vegetables were covered with polyethylene film, under a normal atmosphere. Each of them had a shelf life of 5 days. Trays were obtained from 2 supermarket gondolas, one day after packaging. They were transported refrigerated to the laboratory and opened immediately, mixed and divided into different groups for further study.

Three varieties of salads were analyzed:

A. 10 trays (320 g each) with white cabbage, red cabbage and carrot. B. 10 trays (320 g each) with red cabbage, celery and carrot. C. 10 trays (320 g each) with celery, collard and radicchio.

For each salad variety, contents of trays were mixed and distributed in polypropylene bags stored at 8° C. (500-per bag). These were divided into two groups: inoculated with *E. faecalis* GALT and control without addition of this strain, three bags in each group. Bacterial counts were carried out for each mixture at different times: one day after manufacture (0) and 2, 4, and 7 days later.

For the bacterial count, 25 g of each group of vegetables were mixed with 250 ml of Ringer solution and homogenized during 2 minutes (Stomacher Lab-Blender 400). After tenfold dilutions, counting was carried out in plates by duplicate in different media. For total viable mesophilic aerobic bacteria (TVMAB) casein agar, peptone, glucose, yeast extract was used; for enterococci, fGCTC agar; for lactic acid bacteria, fresh MRS agar with the addition of 0.02% p/v sodium azida and 200 ppm of cycloheximide; for total coliform (TC) and fecal (FC) bacteria: crystal violet-red-neutro-bile-glucose agar, with incubation during 24 h under aerobic conditions, at 37° C. and at 44° C., respectively; for *S. aureus*, base Baird Parker agar with emulsion of egg yolk and tellurite.

Determination of pH was carried out at 0, 2, 4, and 7 days of storage using a portable pH meter (Orion Research, Inc., model 610). Statistical analysis of the data was performed giving priority to the two-factor ANOVA test for group and time. SPSS 10.0 software was used, except for the test of simple effects, performed with Excel.

*E. faecalis* GALT has inhibitory activity against the deteriorating bacterial flora (total coliforms and fecal, staphylococci) present in ready-to-eat vegetables during storage at 8° C.

EXAMPLE V

*E. faecalis* GALT as Biopreservative in Fermented Meat Products

In the food industry, the lactic bacteria used as protecting cultures must be able to adapt to prevailing conditions in the corresponding product and should also have competitive ability. In most meat products, lactic bacteria must tolerate nitrite concentrations and relatively low temperatures.

Enterococci colonize raw food of different animal origin and resist adverse ambient conditions (heat, acid pH, high concentrations of NaCl). In fermented products, enterococci survive and may multiply, thus competing with the bacteria used as "starters".

In fermented meat products, the most important microbiota is comprised by diverse lactobacilli species (*L. sakei*, *L. curvatus*, and *L. plantarum*), coagulase-negative staphylococci and *E. faecium*.

Bacteriocin-producing enterococci strains can play an important role in natural preservation of meat products by controlling the growth of different pathogenic or deteriorating bacteria.

Salamin is characterized as a thin cured dry sausage that has been subjected to partial dehydration process to favor long-term preservation.

The evolution of the most representative bacterial groups was studied during the manufacturing process of home-made salamin in a small establishment near de city of Tandil. Variation of pH and lactic acid were also analyzed.

Two batches of salamin were manufactured: one inoculated with *E. faecalis* GALT and one control batch. The mixture was cold-grinded (−1° C.) and stuffed in collagen casing. Then the salamins were taken to a drying chamber with temperature and moisture controlled at 18-20° C. and 90-95%, respectively, until the pH reached a value of 5.1.

Then the temperature was set at 12-14° C. and the moisture at 70-80% until curing was completed.

Inoculation: salamins were inoculated with 106 UFC/ml *E. faecalis* GALT obtained from an 18 h culture in brain-heart infusion and further centrifugation and washing of bacterial sediment with 8.5 g/l NaCl.

Sampling: sampling for the bacteriologic and lactic acid analysis was carried out at the following times: 0 (after stuffing); end of drying (ED; pH 5.1); 7 days and end of curing (EC; 21 days).

Microbiological Analysis: 15 g aliquots of salamin were homogenized with a "Stomacher 400" (Lab System) during 2 min with 135 ml of sterile diluent (1 g/L bacto-peptone (Disco), 8 g/L NaCl (Merck), pH 7.0). Seeding was performed from a decimal dilution series in different selective media for counting of bacterial groups.

a) Enterobacteriaceae

Deep seeding was performed in crystal violet-red-neutro-bile-glucose agar (VRBG; Merck). After 24 h of incubation at 30° C., violet colonies surrounded by a precipitation haze (positives) were confirmed by Gram staining and cytochrome oxydase and catalase biochemical tests.

b) Micrococcaceae

Agar plates with salt and mannitol (Disco) were used for surface seeding. After incubation (25° C., 4-5 days), colonies were confirmed by Gram staining.

c) *S. aureus*

Petri dishes with Baird-Parker agar and fresh egg-tellurite (Difco) were surface-seeded and incubated at 35° C., 48 h. Black, shiny colonies surrounded by precipitation haze were confirmed by Gram staining and catalase, coagulase, and DNAse assays.

d) *Lactobacillus*

MRS agar plates were deep-seeded (pH 5.4) using the double layer technique. After incubation at 30° C. during 3 days, confirmation of colonies was performed using Gram staining and catalase.

e) *Enterococcus*

Counting was carried out in fGCTC agar, with incubation at 35° C. during 24 h. Confirmation of colonies was performed by Gram staining, catalase, growth at 45° C. and hydrolysis of pyrrolidonyl-beta-naphthylamide.

Phenotypic characterization of *E. faecalis* was carried out for 4 random-selected colonies not showing fluorescence or that did not hydrolyze starch. Monitoring of *E. faecalis* GALT was performed measuring the inhibitory activity against *L. monocytogenes* CEB 101 using the double-layer technique.

A search for plasmids was carried out in recovered *E. faecalis* strains that inhibited the growth of the starter strain.

Determination of pH: pH of samples was determined in similar points of probe insertion (Orion Research Inc.) at time 0 (once stuffing was completed), 15 h, 36 h, 48 h, 60 h, 7 d and 14 d.

Determination of lactic acid: a 5 g sample was thoroughly homogenized in a meat grinder, 20 ml of 1 M perchloric acid was added. It was mixed on magnetic mixer during 10 min and transferred to a beaker containing 40 ml of distilled water, where pH was adjusted to 10-11 with 2N potassium hydroxide, under continuous stirring.

The volume was completed to 100 ml with distilled water. It was cooled during 20 min to separate fats and precipitate potassium perchloride. Finally, it was filtered and determination of lactic acid was performed in solution using the API 50 CHL system (BioMérieux).

For statistical analysis, a two-factor variance analysis was used (group and time). In order to analyze if the variation between different times was group-dependant, the simple effect test was used. The SPSS 10.0 program was employed, except for the test of simple effects, which was performed with Excel. Concentration of enterobacteria turned out to be similar to time zero in both batches. The batch inoculated with *E. faecalis* GALT showed significantly lower values than the control series during the process: ED ($p<0.001$), 7 d ($p<0.001$), and EC ($p<0.001$). Values for *S. aureus* in the inoculated batch were low and also lower than the control: ED ($p<0.05$), 7 d ($p<0.005$), and EC ($p<0.001$). Bacterial load decreased only in the inoculated batch during the stuffing process ($p<0.01$). Bacterial counts of the Micrococcaceae family in the batch inoculated with *E. faecalis* GALT were lower than control for ED time ($p<0.001$) and 7 d ($p<0.01$), but not for other times.

In the case of *Lactobacillus*, no significant differences were recorded in the number of bacteria in both series during the period of aging. Concentration of enterococci in the control group was significantly higher only for time zero ($p<0.01$). In the control group, initial counts increased significantly for ED time and then remained constant ($p<0.05$).

Accordingly, *E. faecalis* GALT is useful as a biopreservative for fermented meat products.

EXAMPLE VI

Another pre-requisite for a successful research and development of probiotics is the knowledge about indigenous intestinal microflora that offers protection against infections, as a disturbance of this flora might increase susceptibility to infections.

*E. faecalis* GALT shows no systemic pathogenic power. When inoculated i.p. in mice, its DL50 value was 1 logarithm lower than that for strains belonging to a collection of *E. faecalis* without known virulence factors.

*E. faecalis* GALT shows no phenotypical expression of virulence factors, it resists gastric pH, produces a broad spectrum enterocine, and it adheres to and persists on intestinal tissue of BALB/c mice.

*E. faecalis* GALT protects against challenges with *Salmonella* enteriditis serotype. The probiotic ability of *E. faecalis* GALT is shown in studies carried out using BALB/c mice (n=10) inoculated i.g. during 6 days with 200 μg of *E. faecalis* GALT ($3\times10^8$ cells/ml) and challenged i.g. with 200 μg of *Salmonella* enteriditis serotype ($5\times10^4$ cells/ml). Animals of the study group and control group (physiologic solution) were observed during 15 days. In intestines of mice from the control group, 8.37 log UFC/g of *S. Enteriditis* serotype were counted and an important displacement of coliform authochtonous bacteria was observed with no detection of *E. coli*. In those who received *E. faecalis* GALT before the challenge, no pathogenic strain was detected (counts in Salmonella-Shigella agar) but presence of enterococci (4.21 log UCF/g) and coliform (7.25 log UFC/g) was observed. These observations are consistent with the death of all mice belonging to the control group and survival of all the animals that received *E. faecalis* GALT. The results show the ability of *E. faecalis* GALT as it was innocuous and protected a 100% of animals against challenge with *S. Enteriditis* serotype.

*E. faecalis* GALT protects against challenges with *E. coli* 0157H7 (using the same model).

*E. faecalis* GALT protects against challenges with *Shigella sonnei* (using the same model).

*E. faecalis* GALT protects against challenges with *Shigella fexneri* (using the same model).

*E. faecalis* GALT protects against challenges with eggs from *Toxocara canis*.

Ten male Swiss mice were used for each group of inoculated and control. Obtention of embryonated *Toxocara canis* eggs: eggs were incubated in a solution of 0.1N sulphuric acid and 1% formalin during 40 days at room temperature (Oshima technique, 1976). Challenge was performed inoculating mice with 100 embryonated *T. canis* eggs.

Mice were sacrificed 48 h after the challenge. The intestinal implant of *E. faecalis* GALT was analyzed, as described for the previous protocol, and the presence of *T. canis* in lung was investigated. No *T. canis* was detected in lungs of mice protected with *E. faecalis* GALT.

EXAMPLE VII

Modulation Studies for Specific Immune Response a) Inhibition Assays for Proliferation of T lymphocytes It is well-known that there exist differences between the action of commensal and pathogenic bacteria on cells from the immune system. Common bacteria from the intestinal tract do not stimulate proliferation of mononuclear cells and play an important role in maintaining hyporeactivity to foreign antigens. On the contrary, pathogenic bacteria activate immune cells present in their entrance pathway and therefore favor their proliferation and triggering of an inflammatory reaction.

When the activity of *E. faecalis* GALT on a culture of splenic T lymphocytes was analyzed in BALB/c mice, the proliferative level of Concavaline A (ConA, mitogen) stimulated lymphocytes was higher than when stimulated with a mixture of *E. faecalis* GALT and Con A ($p<0.001$). These results show the inhibitory activity of *E. faecalis* GALT on the proliferative action of the Con A mitogen on T lymphocytes.

b) Cytokine Induction Assays

*E. faecalis* GALT induces production of pro-inflammatory as well as anti-inflammatory type cytokines on a culture of peritoneal macrophages.

An efficient control of microbial infections not only requires immune activation after pathogenic invasion, but also demands the onset of appropriate unique immune responses generated for a certain group of pathogens. Thus, certain infections require Th1-type responses, while others may be better controlled with a Th2-type immunity. Antigen presenting cells (dendritic, macrophages, and others) may adjust the balance of Th1-Th2 according to the results of their interactions with cytokine IL-10 and IL-12 differentially producing-microbes. IL-10 is related to the priming of Th2 response, while IL-12 potentially induces interferon-gamma producing Th1 cells (INF-γ).

In order to examine the stimulating effect of *E. faecalis* GALT on peritoneal macrophages in culture, the ability of these cells to produce pro-inflammatory and anti-inflammatory cytokines was evaluated. The presence of IL-6, IL-10, and IL-12p40 (ELISA) was evaluated in supernatants of cultures stimulated with *E. faecalis* GALT ($5 \times 10^5$-$5 \times 10^7$ cells/ml) and incubated for 24 hours at 37° C. and 5% of $CO_2$.

*E. faecalis* GALT induced, depending on stimulus concentration, the production of IL-10, IL-12, IL-6, but no of IL-18. The results achieved indicate that *E. faecalis* GALT is an excellent candidate to be used as a modulator of the immune response as it induces production of IL-12 (inflammatory response) as well as of IL-10 (anti-inflammatory response).

*E. faecalis* GALT, when preadministered intragastrically in mice further immunized with bacterial vaccines (Diphtheria-Tetanus-Pertussis), induces an increase of the proliferative response memory of specific T lymphocytes by stimulating the production of type Th1 (INF-γ) and Th2 (IL-5) cytokines.

c) Inhibition of Proliferation of Myeloma Cell Line Assays.

The effect of *E. faecalis* GALT on the proliferation of myeloma cell line P3×63-Ag8.653 (tumoral cells) and Vero cells was comparatively established. The myeloma cell line P3×63-Ag8.653 was grown in RPMI1640 medium supplemented with 15% of bovine fetal serum, 50 IU ml$^{-1}$ of penicillin, 50 mg ml$^{-1}$ of streptomycin and 1% of L-glutamine. Vero cells were grown in Dulbeccois Modified Eagle medium supplemented with 10% bovine fetal serum, 50 IU ml$^{-1}$ of penicillin, 50 mg ml$^{-1}$ of streptomycin and 1% of L-glutamine. Cell cultures were incubated at 37° C. and 100% of humidity in an atmosphere with 5% of $CO_2$. A cell proliferation kit (Roche Molecular Biochemicals) was used to study strain effect of the strains ($10^6$, $10^7$ and $10^8$ UFC ml-1) on myeloma cell proliferation. The MTT assay was performed in 48-well microtiter plates and the optic density of each well was measured at 620 and 690 nm. The results were satistically analyzed.

The results of the MTT assays showed that, independently from the dose employed, the *E. faecalis* GALT strain did not modify the proliferation level of Vero cells. However, *E. faecalis* GALT inhibits proliferation of myeloma cells up to a 75%, in a direct dose-dependant fashion of bacteria used in the MTT assay.

d). Immunomodulatory Effect

The effect of *E. faecalis* CECT7121 on proliferation of murine LBC T lymphoma was analyzed. To this end, LBC cells ($5.10^5$ cells/ml, 100 ul) were incubated with an equal volume of RPMI (control), heat-killed *E. faecalis* CECT7121, heat-killed *E. faecalis* CECT7121 without plasmid (cured *E. faecalis* CECT7121) both in a range of concentrations of $5.10^2$-$5.10^8$ UFC/ml, o with an *E. faecalis* CECT7121 lysate (20 μg/ml). Cell proliferation was determined by incorporation of $^3$H thymidine after 24 hs of culture. LBC cell proliferation was inhibited by the *E. faecalis* CECT7121 lysate (p<0.05, ANOVA), by *E. faecalis* CECT7121 at $5.10^\circ$-$5.10^8$ UFC/ml (p<0.01) and by cured *E. faecalis* CECT7121 $5.10^8$ UFC/ml (p<0.01, ANOVA). The correlation between the observed inhibition of proliferation and induction of apoptosis was verified using agarose gels for detecting nucleosomal DNA fragmentation and staining with acrydine orange and ethidium bromide. These results indicate that *E. faecalis* CECT7121 has an antiproliferative effect on the LBC cell line and induces apoptosis of tumoral cells. This effect would be mediated not only by the structure of the *E. faecalis* CECT7121 cell wall, but also to some extent by plasmid-encoded molecules.

EXAMPLE VIII

Vehiculization of *E. faecalis* CECT7121 Bacteriocin for its Addition to Food

In order to consider Bacteriocin production useful at industrial level, it is considered essential that the growing substrate for the production strain for producing said bacteriocin is of food grade and low cost. Based on this, subproducts from the dairy industry may be used as alternative growth and production media.

Development and production of bacteriocin in lactoserum and lactalbumin (from cheese manufacturers and commercial lyophilizates) were tested in *E. faecalis* CECT7121

Drying (electrospray, ultrafiltration) of preparations was also performed in order to achieve a greater stabilization of the same.

Formulations:
Production of bacteriocin in:
Lactoserum
Lactalbumin

It was established that lactoserum (LS) is a suitable medium for the development and production of bacteriocin in *E. faecalis* CECT7121. Optimal production conditions are achieved when LS is heated to 110° C. during 10 min before its use. Other conditions that favor bacteriocin production is the addition of 1% glucose and any type of 0.25% peptone. The optimal initial inoculum of the strain in LS is of 4%, with incubation for 18 h at 30° C. without stirring.

Optimal production was achieved with 5% lactalbumin supplemented with 1% glucose, pH stabilized at 6.60 without addition of peptone. The initial inoculum is of 8%, with incubation during 18 h, no stirring.

Although some embodiments and preferred embodiments of the invention are described herein, said embodiments should only be considered as illustrative. It should be evident for those skilled in the art that modifications may be made without departing from the spirit of the invention and the scope of the appended claims.

BIBLIOGRAPHY

Dice L R. Measures of amounts of ecologic association between species 1945 Ecology 26: 297-302.

Merquior V L C, Peralta J M, Facklam R R, Teixeira L M 1994 Analysis of electrophoretic whole-cell protein profiles as a tool for characterization of *Enterococcus* species. *Curr Microbiol*, 28:149-153.

Persing, D. H., Smith, T. F., Tanover, F. C. and White, T. J. 1993. Diagnostic Molecular Biology, Principles and Application. Washington D.C.: ASM.

Suzzi G, Caruso M, F. Gardini, A. Lombardi, L. Vannini, M. E. Guerzoni, C. Andrighetto and M. T. Lanorte. 2000. A survey of the enterococci isolated from an artisanal Italian goat's cheese (semicotto caprino) J. Appl. Microbiol., 89, 267-274.

The invention claimed is:

1. An isolated strain of *Enterococcus faecalis* GALT deposited in The Spanish Collection of Type Cultures, 46100 Burjassot (Valencia) Spain, as *E. faecalis* CECT7121.

2. The strain of *E. faecalis* GALT and/or a culture supernatant and/or Peptide (AP)-CECT7121 according to claim 1, characterized in that they do not show in vitro multiresistance to antibiotics administered.

3. The strain *E. faecalis* GALT and/or a culture supernatant and/or Peptide (AP)-CECT7121 according to claim 1, characterized in that it does not have red blood cell-destroying hemolysines of human, bovine and equine origin, and it does not produce gelatinase, DNAse, and decarboxylases.

4. The strain of *E. faecalis* GALT and/or a culture supernatant and/or Peptide (AP)-CECT7121 according to claim 1, characterized in that it shows inhibitory action on Gram-positive multiresistance strains selected from *Listeria monocytogenes, Staphylococcus aureus, Streptococcus pneumoniae, Enterococcus faecalis, E. faecium, E. durans, E. gallinarumcasseliflavus, Str. agalactiae, Str. dysgalactiae, Str. uberis, Clostridium perfringens, C. sporogenes, Bacillus subtilis,* and *B. cereus.*

5. The strain of *E. faecalis* GALT and/or a culture supernatant and/or Peptide (AP)-CECT7121 according to claim 4, characterized in that it further shows inhibitory activity of Gram-negative strains.

6. A bioprotective food composition containing a bioprotectively effective amount of the isolated *E. faecalis* GALT strain and/or a culture supernatant thereof and/or Peptide (AP)-CECT7121 according to any one of claims 1-3 and 4-5, together with an edible carrier or a pharmaceutical matrix.

7. A probiotic containing a therapeutically effective amount of the isolated *E. faecalis* GALT strain and/or a culture supernatant thereof and/or Peptide (AP)-CECT7121 according to any one of claims 1-3 and 4-5, for the treatment and/or prophylaxis of disorders associated with colonization by pathogenic microorganisms of the gastrointestinal tract of humans and/or animals.

8. A probiotic containing an effective amount of the isolated *E. faecalis* GALT strain and/or a culture supernatant thereof and/or Peptide (AP)-CECT7121 according to any one of claims 1-3 and 4-5, for improving health or comfort of the gastrointestinal tract of humans and/or animals.

9. A probiotic containing an effective amount of the isolated *E. faecalis* GALT probiotic strain and/or a culture supernatant thereof and/or Peptide (AP)-CECT7121 according to any one of claims 1-3 and 4-5, for the regulation of the immune response in humans and/or animals.

10. The strain of *E. faecalis* GALT and/or a culture supernatant and/or Peptide (AP)-CECT7121 according to claim 2, wherein the antibiotics are glycopeptides selected from the group consisting of vancomycin and teicoplanine; or carbapenemes selected from the group consisting of: impipenem, meropenem; and ampicillin.

11. The strain of *E. faecalis* GALT and/or a culture supernatant and/or Peptide (AP)-CECT7121 according to claim 5, wherein the Gram-negative strains are strains selected from the group consisting of: *E. coli, Shigella sonnei,* and *Shigella flexneri.*

* * * * *